US011819264B2

(12) United States Patent
Brockmann et al.

(10) Patent No.: US 11,819,264 B2
(45) Date of Patent: Nov. 21, 2023

(54) DETACHABLE INSULATING INSERT FOR USE IN A RESECTOSCOPE

(71) Applicant: OLYMPUS WINTER & IBE GMBH, Hamburg (DE)

(72) Inventors: Christian Brockmann, Hollenstedt (DE); Andreas Offt, Reinbek (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 537 days.

(21) Appl. No.: 16/775,723

(22) Filed: Jan. 29, 2020

(65) Prior Publication Data

US 2020/0246062 A1    Aug. 6, 2020

(30) Foreign Application Priority Data

Feb. 5, 2019   (DE) .......................... 102019102841.8

(51) Int. Cl.
*A61B 18/14*   (2006.01)
*A61B 1/00*    (2006.01)
*A61B 1/002*   (2006.01)
*A61B 18/00*   (2006.01)

(52) U.S. Cl.
CPC .......... *A61B 18/149* (2013.01); *A61B 1/002* (2013.01); *A61B 1/00087* (2013.01); *A61B 2018/00083* (2013.01); *A61B 2018/00601* (2013.01); *A61B 2018/00982* (2013.01)

(58) Field of Classification Search
CPC ............. A61B 18/149; A61B 1/00087; A61B 1/002; A61B 2018/00083; A61B 2018/00196; A61B 2018/00601; A61B 2018/00982; A61B 2018/1407; A61B 2018/144; A61B 2018/1475

USPC .......................................................... 606/46
See application file for complete search history.

(56) References Cited

U.S. PATENT DOCUMENTS

| 5,196,011 | A | 3/1993 | Korth et al. |
| 5,408,992 | A | 4/1995 | Hamlin et al. |
| 5,423,813 | A | 6/1995 | Kaiser et al. |
| 6,068,603 | A * | 5/2000 | Suzuki .................. A61B 10/04 |
| | | | 600/564 |
| 6,149,620 | A | 11/2000 | Baker et al. |
| 7,150,745 | B2 | 12/2006 | Stern et al. |

(Continued)

FOREIGN PATENT DOCUMENTS

| DE | 10122465 C1 | 8/2002 |
| DE | 102006053338 A1 | 5/2008 |

(Continued)

OTHER PUBLICATIONS

U.S. Appl. No. 16/775,496, filed Jan. 29, 2020 in the name of Christoph Knopf.

(Continued)

*Primary Examiner* — Michael F Peffley
(74) *Attorney, Agent, or Firm* — Oliff PLC

(57) ABSTRACT

An electrically insulating insert for detachable connection to the distal end region of a resectoscope shaft, characterized in that the insulating insert has a hollow portion with an elongate cavity for the passage of pass-through instruments, and that the insulating insert has fastening means for detachable connection to the resectoscope shaft. An electrode instrument is connected to this insulating insert and to a resectoscope including the same.

9 Claims, 4 Drawing Sheets

(56) References Cited

U.S. PATENT DOCUMENTS

| | | | |
|---|---|---|---|
| 7,261,711 B2 | 8/2007 | Mulier et al. | |
| 7,303,561 B2 * | 12/2007 | Ouchi | A61B 18/1492 606/45 |
| 7,347,860 B2 * | 3/2008 | Ouchi | A61B 18/1492 606/46 |
| 7,572,251 B1 | 8/2009 | Davison et al. | |
| 7,815,639 B2 * | 10/2010 | Brommersma | A61B 1/307 606/45 |
| 9,072,443 B2 * | 7/2015 | Hashido | A61B 1/00089 |
| 2002/0111608 A1 | 8/2002 | Baerveldt et al. | |
| 2002/0188293 A1 | 12/2002 | Manzo | |
| 2002/0193792 A1 | 12/2002 | Valencic et al. | |
| 2003/0144605 A1 | 7/2003 | Burbank et al. | |
| 2003/0187324 A1 | 10/2003 | Gatto | |
| 2004/0044343 A1 | 3/2004 | Brommersma et al. | |
| 2005/0080412 A1 | 4/2005 | Ouchi | |
| 2006/0030844 A1 | 2/2006 | Knight et al. | |
| 2006/0069303 A1 | 3/2006 | Couvillon | |
| 2007/0093812 A1 | 4/2007 | Hayashida et al. | |
| 2009/0043303 A1 | 2/2009 | Shimomura | |
| 2009/0270859 A1 | 10/2009 | Hirvi | |
| 2012/0095458 A1 | 4/2012 | Cybulski et al. | |
| 2012/0197245 A1 | 8/2012 | Burnett et al. | |
| 2013/0218243 A1 | 8/2013 | Schomacker et al. | |
| 2013/0226165 A1 | 8/2013 | Manwaring et al. | |
| 2014/0171824 A1 | 6/2014 | Hugle et al. | |
| 2014/0236143 A1 | 8/2014 | Ward | |
| 2014/0379055 A1 | 12/2014 | Schomacker et al. | |
| 2015/0005799 A1 | 1/2015 | Lindquist et al. | |
| 2015/0011993 A1 | 1/2015 | Horlle | |
| 2015/0327753 A1 | 11/2015 | Amirana et al. | |
| 2015/0351826 A1 * | 12/2015 | Kroeber | A61B 1/00087 600/105 |
| 2016/0038028 A1 | 2/2016 | Buelna et al. | |
| 2016/0120599 A1 | 5/2016 | Amirana et al. | |
| 2016/0192983 A1 | 7/2016 | Klink et al. | |
| 2017/0014202 A1 | 1/2017 | Ransbury et al. | |
| 2017/0071664 A1 | 3/2017 | Lim | |
| 2019/0038341 A1 | 2/2019 | Brockmann et al. | |
| 2020/0121791 A1 | 4/2020 | Zamadar | |

FOREIGN PATENT DOCUMENTS

| | | |
|---|---|---|
| DE | 102013001156 A1 | 7/2014 |
| DE | 102017117749 A1 | 2/2019 |
| EP | 1221903 B1 | 6/2006 |
| EP | 1 974 683 A1 | 10/2008 |
| EP | 3 437 581 A1 | 2/2019 |
| WO | 2017/161331 A1 | 9/2017 |

OTHER PUBLICATIONS

U.S. Appl. No. 16/775,572, filed Jan. 29, 2020 in the name of Christoph Knopf.
U.S. Appl. No. 16/811,675, filed Mar. 6, 2020 in the name of Christian Brockmann et al.
Gerhard Lanzer. "Grundzüge Des Eisenstoffwechsels [Fundamentals of Iron Metabolism]". Klinik, 2010, vol. 6, pp. 43-46.
Sep. 17, 2021 Office Action issued in U.S. Appl. No. 16/775,496.
Apr. 8, 2022 Final Office Action Issued in U.S. Appl. No. 16/775,496.
Dec. 8, 2021 Office Action issued in U.S. Appl. No. 16/811,675.
Jul. 13, 2022 Office Action Issued In U.S. Appl. No. 16/775,572.
May 12, 2022, Office Action issued in U.S. Appl. No. 16/811,675.
Mar. 3, 2023 Office Action Issued in U.S. Appl. No. 16/811,675.
Sep. 8, 2023 Office Action issued in U.S. Appl. No. 16/811,675.

\* cited by examiner

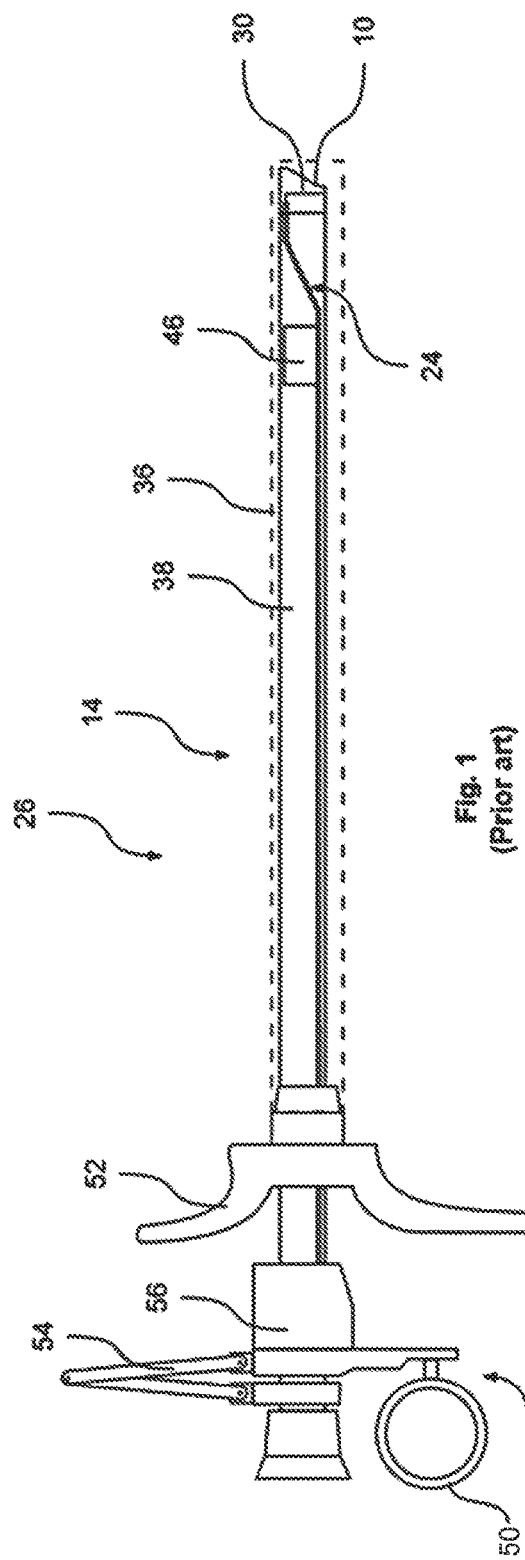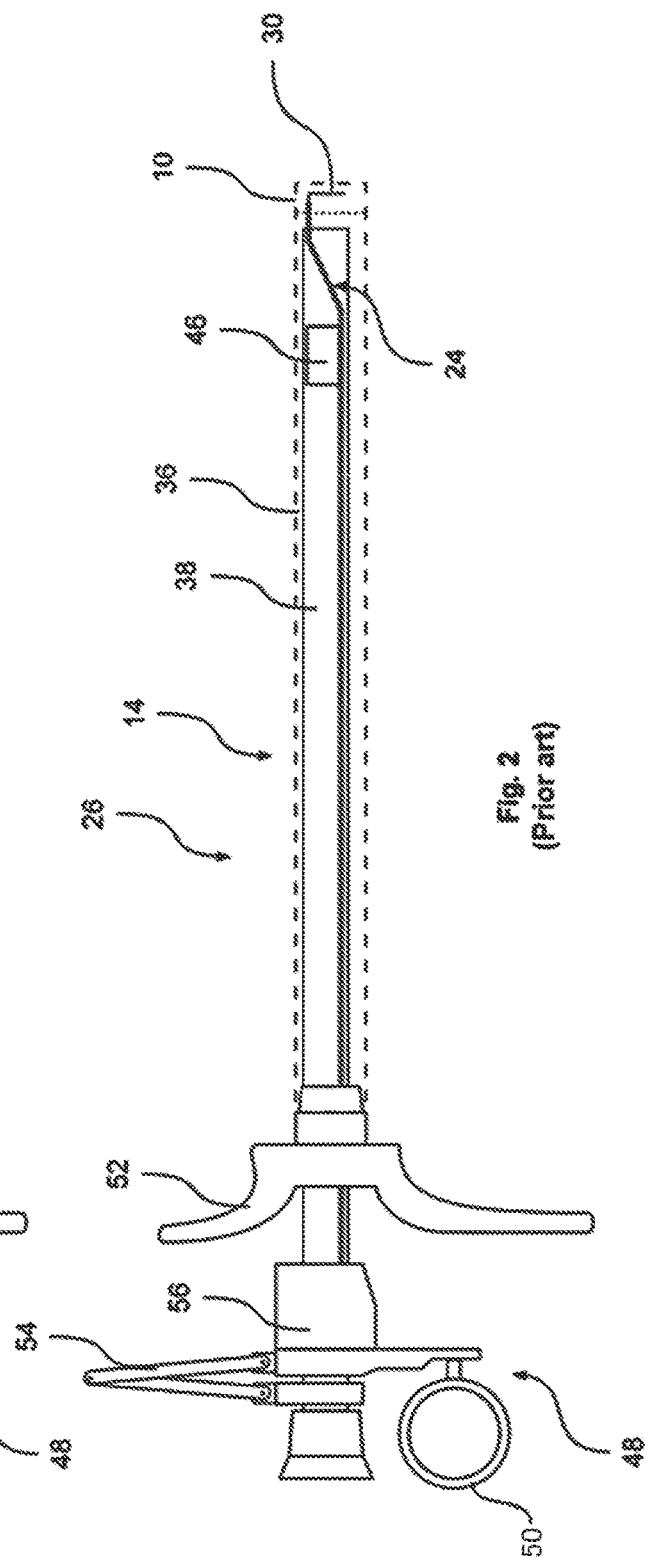

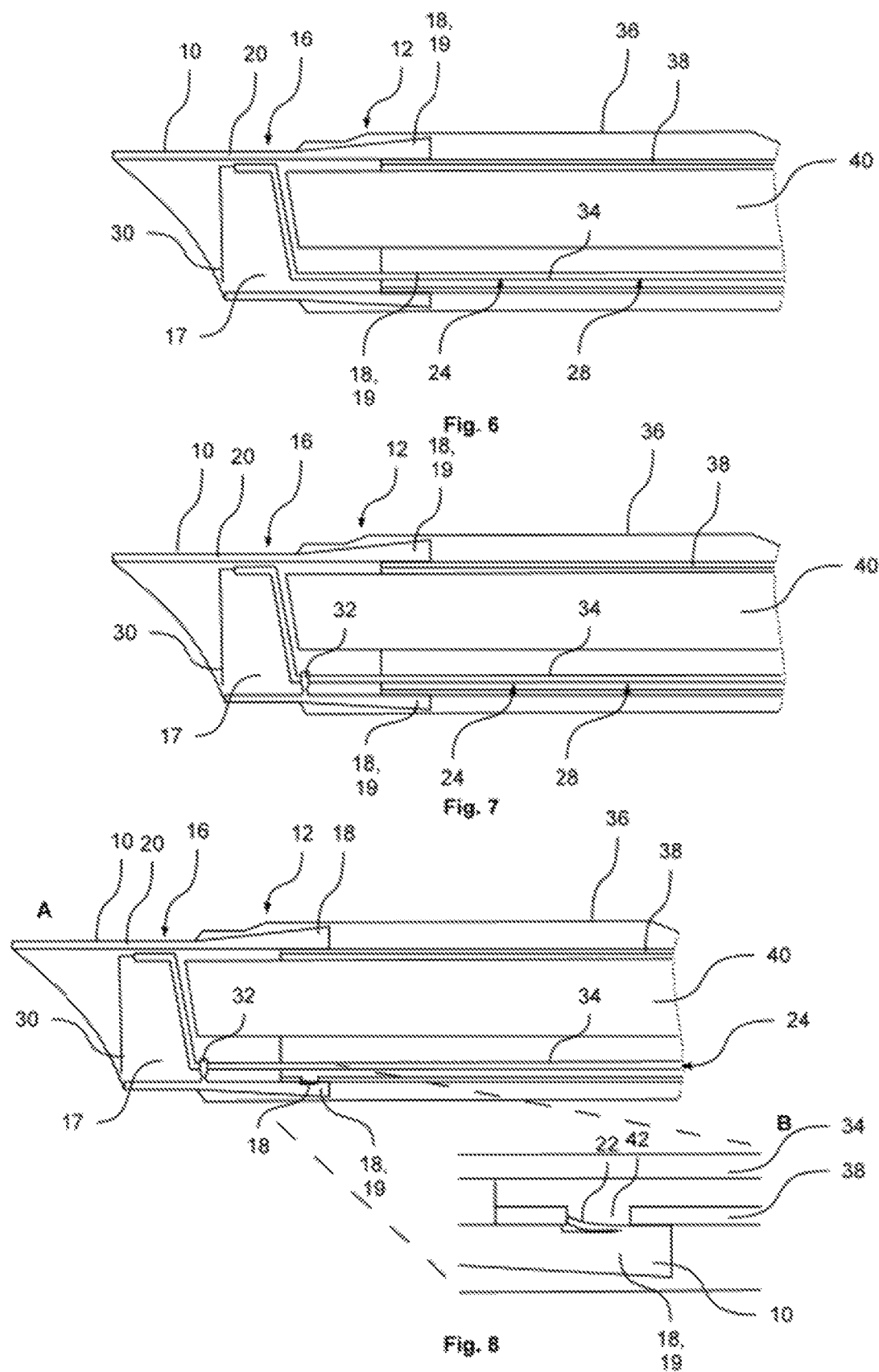

DETACHABLE INSULATING INSERT FOR USE IN A RESECTOSCOPE

BACKGROUND

The invention relates to an electrically insulating insert and to an electrode instrument and to a resectoscope.

Resectoscopes of the generic type, which have corresponding electrode instruments and an insulating tip at their distal end, are used primarily in urology for electrosurgical work in the bladder and urethra. They are usually used for resection and vaporization of tissue, for example tissue in the lower urinary tract. For this purpose, the resectoscopes used comprise a longitudinally displaceable electrosurgical pass-through instrument which, after insertion of the resectoscope, can be pushed with its distal working end out of the distal end of the shaft tube of the resectoscope. The electrosurgical pass-through instrument can comprise an electrosurgical electrode at its distal working end, for example in the form of a loop or vaporization button (e.g., PlasmaButtons). Examples of such instruments include the OES PRO resectoscopes (Olympus) or other continuous-irrigation resectoscopes per Iglesias.

In order to prevent short circuits between the active electrode and the conductive material of the shaft tube, the resectoscopes usually comprise a portion in their distal end region that is made of an insulating material such as a ceramic and is usually referred to as an insulating tip or an insulating insert. As is shown in FIGS. 1 and 2, the insulating insert can either be arranged on the inner shaft (FIG. 1) or on the outer shaft (FIG. 2). Since the resectoscope is designed for multiple use and must therefore also withstand sterilization conditions such as autoclaving, for example, the insulating insert must meet high requirements in terms of durability and reconditionability in both cases. The choice of materials is therefore usually limited to relatively expensive, high-performance ceramics such as silicon nitrite. In order to minimize the fragility of insulating inserts that are made of ceramic, the inserts must also have a relatively high wall thickness.

It would be desirable to be able to both reduce the cost of the insulating inserts and further reduce their wall thicknesses. A need therefore exists for correspondingly improved insulating inserts.

DESCRIPTION

This object is achieved by an insulating insert as disclosed herein, an electrode instrument as disclosed herein, and a resectoscope as disclosed herein. According to the invention, the insulating insert is designed in particular as a part for single use that is detachably connected to the resectoscope shaft and can therefore be replaced in a simple manner after use and replaced by a new insulating insert. At the same time, the insulating insert is held securely on the resectoscope shaft by means of a fastening means, whereby loss of the insulating insert during an operation is excluded.

In a first aspect, the invention therefore relates to an electrically insulating insert for detachable connection to the distal end region of a resectoscope shaft, characterized in that the insulating insert has a hollow portion with an elongate cavity for the passage of pass-through instruments, and that the insulating insert has fastening means for detachable connection to the resectoscope shaft.

The insulating insert is electrically non-conductive, i.e., electrically insulating. The insulation of the active electrode from the conductive resectoscope shaft is thus ensured. For this purpose, the insulating insert is preferably made completely—or at least to an extent that ensures the insulating ability of the insert—of an electrically non-conductive, i.e., electrically insulating, material. Such materials are known to those skilled in the art and include ceramics and plastics, for example. Insulating inserts made of plastics are especially preferred according to the invention due to their relatively low production costs and good insulating properties. Since the insulating insert can come into contact with the plasma that is produced when used during an electrosurgical treatment with an electrode, thermostable plastics are particularly preferred. Thermostable plastics are able to withstand the high temperatures in the vicinity of the distal resectoscope tip without damage. Suitable thermostable plastics can be selected, for example, from the group consisting of fluoropolymers and cycloolefin copolymers. The insulating inserts made of plastic can be manufactured by means of an injection molding process.

The insulating insert is suitable for detachable connection to the distal end region of a resectoscope shaft. This means that the insulating insert and the end region are complementary to one another in terms of shape and size. This enables the insulating insert to be connected to the end region. Various possible embodiments for this connection are described elsewhere herein. In any case, the connection is fixed or secured in such a way that detachment of the insulating insert is prevented during an operation.

At the same time, the connection between the resectoscope shaft and the insulating insert is designed to be detachable in order to enable easy replacement and/or cleaning of the insulating insert, for example by the medical specialist or the cleaning specialist responsible for reconditioning the instrument—i.e., the end users of the resectoscope. In particular, the insulating insert is therefore not glued to the end region of the resectoscope shaft. However, this does not exclude the possibility that the removal of the connection between the insulating insert and the resectoscope shaft may require standard disassembly steps for cleaning. For instance, it is necessary in certain embodiments of the invention to detach the outer shaft (cladding tube) from the inner shaft with inserted electrode instrument before the insulating insert can be detached from the inner shaft or the outer shaft.

The connection between the resectoscope shaft and the insulating insert is established in the distal end region of the shaft. As a rule, the insulating insert will be designed at least in some portions to be complementary in shape to the elements of the resectoscope shaft that are arranged in its end region. For instance, the insulating insert, which has a cylindrical portion, can be pushed onto the inner or outer tube, inserted into the inner tube, or inserted between the inner and outer tube. The latter option is preferred. The insulating insert can be connected to the inner tube, for example, and shaped such that the inner tube connected to the insulating insert can be inserted into an outer tube from the proximal direction.

In the assembled state, the insulating insert and the resectoscope shaft therefore usually overlap, meaning that they engage with one another. As will readily be understood, in order to ensure adequate insulation of the electrode, the insulating insert should not be fully inserted into the resectoscope shaft. Starting from the distal end of the resectoscope shaft, the overlapping region—and thus the "distal end region"—of the abovementioned resectoscope shaft will therefore generally be limited to a distal portion of a few mm, e.g., 10 mm or less, 8 mm or less, preferably 5 mm or less.

As mentioned, the insulating insert has a hollow portion with an elongate cavity for the passage of pass-through instruments. This portion is arranged in the proximal end region of the insulating insert. It ensures that pass-through instruments that are guided through the resectoscope shaft can be guided through the channel-shaped interior of the insulating insert. The insulating insert can have a substantially cylindrical shape or at least one substantially cylindrical proximal portion. Accordingly, the cavity in the interior of the hollow portion can have a hollow cylindrical shape. However, it is also envisaged in the context of the invention to design the cavity and the corresponding portion so as to have non-circular cross sections. For certain applications, it can be advantageous for the cavity and/or the outside of the portion to be designed with an elliptical or oval-shaped cross section. Irregular cross sections are also conceivable, such as indentations or protuberances in the inner wall of the portion for guiding certain pass-through instruments. Moreover, it has been contemplated that the wall thickness of the portion be adapted to its respective load. For example, the wall can be made thicker in a distally extended region than the wall in other regions of the insulating insert. Overall, the hollow portion can be regarded as being tubular, with the term "tube," as described previously, not only encompassing purely hollow cylindrical shapes, but elongate portions having an outer wall and an elongate cavity inside, with the cavity being open at its distal and proximal ends in order to allow pass-through instruments to pass through. "Pass-through instruments" to be passed through can include electrode instruments, optics, irrigation tubes, and the like.

Otherwise, the insulating insert can have customary shapes, particularly in its distal end region. The walls of the insulating insert are preferably arranged in the wall space of a hollow cylindrical space. However, as indicated above, different wall thicknesses are also permitted within the scope of the invention. The wall space preferably has the same inner diameter as an inner tube arranged in the resectoscope shaft. In the past, the shape that is shown in FIG. 1 in particular, which is distally extended on one side for insulating tips, has been found to be advantageous. The distally extended region and the region of the hollow portion located proximally thereof can have a greater wall thickness than other regions of the insulating insert. With such "beak-shaped" insulating inserts, tissue can be supported on the extended side of the insert, so that the tissue cannot fall into the field of vision. In addition, this design extends the path of the irrigation fluid and thus generates a rectilinear stream that reduces the risk of turbulence in front of the optics. At the same time, the electrode can continue to cut tissue close to the edge of the insulating insert.

According to the invention, the insulating insert has one or more fastening means for releasable connection to the resectoscope shaft. The fastener or fasteners can take various forms and, in conjunction with the formation of the distal end region of the resectoscope shaft, ensures a secure but releasable connection. The fastening means are generally arranged in the proximal end region of the insulating insert, preferably in the hollow portion thereof.

The fastening means can, for example, comprise or consist of a radial thickening of the insulating insert in its hollow portion. The thickening can be in engagement with another element on the resectoscope shaft and thereby secure the insulating insert against displacement in the distal direction. The other element on the resectoscope shaft can be an engagement opening or a protrusion, for example. The thickening can be flexible and embodied as a snap element, for example, in order to enable the insulating insert to be pushed onto the resectoscope shaft. Alternatively, the thickening can be inflexible if, for example, the insulating insert is arranged between structures of the inner tube and the outer tube when the resectoscope is mounted.

The radial thickening can consist, for example, in a) a larger outer diameter of the insulating insert relative to the outer diameter at the distal end of the hollow portion, and/or b) a larger diameter of the wall of the insulating insert relative to the diameter of the wall at the distal end of the hollow portion. In an example of a larger outer diameter according to alternative a), the insulating insert, particularly the outer wall thereof, can be completely or partially conical in the axial direction. The outer diameter of the insulating insert at its proximal end would then be larger than its outer diameter at its distal end. In an example of a larger diameter of the wall of the insulating insert according to alternative b), one or more protrusions, for example in the form of pins, can be formed on the outer or inner wall of the insulating insert. The protrusion can be formed radially along a periphery of the corresponding wall or as one or more pins that are arranged radially along a periphery of the corresponding wall.

Alternatively or in addition, the fastening means can comprise or consist of a part of a connection that is standard in other areas. For instance, the fastening means can comprise or consist of part of a bayonet, screw, snap, clamp, or locking connection. The corresponding complementary part(s) of the respective connection will then be formed on the resectoscope shaft, so that a bayonet, screw, snap, clamp, or locking connection is formed between the insulating insert and the resectoscope shaft.

In one embodiment, the fastening means comprises a protruding locking element that is arranged on the fastening side of the hollow portion, for example. The "fastening side" is taken here to mean that of the outside and inside of the hollow portion of the insulating insert on which the fastening means is arranged. The fastening side of the hollow portion is preferably the outer wall thereof. This means, for example, that in a region of the insulating insert that is located between the outer tube and the inner tube of the resectoscope shaft, the outer tube has elements for securing the insulating insert against distal displacement.

While the insulating insert is secured against axial displacement, it can be arranged rotatably on the inner or outer tube or between the inner and outer tube in certain embodiments. This enables the insulating insert to rotate during an intervention, so that tissue can be reached from different directions. The rotation of the insulating insert can be synchronized or coupled with the rotation of the electrode about the longitudinal axis of the resectoscope shaft.

In a related, second aspect, the invention relates to an electrode instrument for use in a resectoscope, the electrode instrument having a shaft portion and, at its distal end, an electrode to which high-frequency current can be applied, characterized in that the electrode instrument is connected to an insulating insert according to the invention and the electrode instrument and the insulating insert can be displaced axially relative to one another.

The electrode instruments used in resectoscopes are often designed for single use. The insulating insert according to the invention can also be designed for single use. The aforementioned connection between the electrode instrument and the insulating insert advantageously makes it possible to offer two components of the system that are potentially designed for one-time use and can be replaced together. In addition, the insulating insert can also aid in guiding and positioning the electrode in the shaft system. At the same time, the loop of the electrode can be aligned more precisely with the insulating insert. In addition, the insulating insert can be used as a handle body—i.e., as a body on which the connected parts can be gripped—upon insertion of the electrode instrument that is connected to the insulating insert. This protects the electrode instrument, particularly the electrode, during insertion, and improves the handleability for the end user.

The electrode instrument has an elongate shaft portion (shaft part) and is embodied as a passage instrument for a resectoscope, i.e., as an instrument that can be inserted into a body opening through a resectoscopic shaft tube. At its distal end, the electrode instrument has an electrode to which high-frequency current can be applied. The electrode can be a cutting loop, a plasma button, or other commercially available electrodes. The electrode is preferably a cutting loop electrode. Such electrodes and electrode instruments are known to those skilled in the art.

The electrode instrument can be a bipolar electrode instrument that includes the electrode as part of an electrode assembly. In that case, the electrode instrument will, for example, comprise a second electrode in the distal end region of the electrode instrument that is embodied as a neutral electrode. Alternatively, the second electrode (neutral electrode) can also be arranged on other elements of the distal end region of the resectoscope. As will readily be understood, the electrode instrument can also be designed as a monopolar instrument.

The electrode instrument is longitudinally displaceable within the shaft of a resectoscope, meaning that it can be moved distally and proximally in the axial direction. For connection to the resectoscope, the electrode instrument has at least one elongate shaft that can be fastened at its proximal end to a slide that is encompassed by the resectoscope in order to produce a movement-coupled connection. The slide typically slides on a tube and is spring biased by a spring unit into a rest position. The electrode at the distal end can thus be moved toward or away from tissue to be resected without the need to move the entire resectoscope. Moreover, the longitudinal displaceability of the electrode instrument makes it possible to clamp tissue between the electrode and the insulating insert and remove it from the site of intervention. The distal end of the insulating insert and the electrode can thus be moved toward and away from one another by virtue of the longitudinal displaceability of the electrode instrument.

According to the invention, an electrode instrument that is connected to an insulating insert according to the invention is particularly. The axial longitudinal displaceability of the electrode instrument and insulating insert relative to one another is not prevented by this connection. Instead, the connection ensures longitudinal displacement by a certain distance in the axial direction. The distance includes the distance by which the electrode instrument can usually be moved in the axial direction. At the same time, the connection reduces or prevents mobility in other directions.

The insulating insert can have one or more, preferably two connecting elements, for example, in each of which a fork tube of the electrode instrument is mounted so as to be axially displaceable. The connecting element can be arranged on the inner wall of the insulating insert. In order to reduce the cost of materials and to optimize the fit, the connecting element or elements can be integrally formed with the insulating insert, for example as an injection-molded part. Since the electrode instruments preferably have two fork tubes, it is preferred that the insulating insert have two connecting elements in which these fork tubes can each be supported. The longitudinal axis of the connecting elements thus extends parallel to the longitudinal axis of the insulating insert. The connecting elements are thus connected via their outer wall to the inner wall of the insulating insert. The connecting elements can be tubular, i.e., have a hollow cylindrical shape. As an alternative to these fully tubular connecting elements, the use of partially cylindrical connecting elements—i.e., connecting elements with a partially circular cross section—is also possible within the scope of the invention. The connecting elements can be instantiated as clips or clamps, for example.

In a further, related aspect, the invention relates to a resectoscope for endoscopic surgery with a tubular resectoscope shaft that comprises an elongate cladding tube and an inner tube that is arranged in the cladding tube, as well as rod-shaped optics, characterized in that the resectoscope a) has an insulating insert according to the invention and an electrode instrument with a shaft portion and with an electrode at its distal end to which high-frequency current can be applied to; or b) has an electrode instrument according to the invention.

The resectoscopes according to the invention can be used in all areas of endoscopic surgery. They are particularly well suited for use in narrow body canals such as the urethra. For this purpose, the resectoscopes have the already-described tubular resectoscope shaft. In the usual manner, the shaft can have a cladding tube (outer tube) and an elongate inner tube that extends through the cladding tube, with the electrode instrument that is used according to the invention preferably being arranged in the inner tube. As already indicated above, the wall of the insulating insert according to the invention in its proximal end region is preferably arranged between the cladding tube and the inner tube running inside the cladding tube.

The resectoscope according to the invention also has optics, i.e., an optical image bundle, for viewing the area of intervention and monitoring the intervention. The optics run through the shaft over its length and are also arranged in the inner tube, for example. The optics can comprise an ordered fiber bundle and/or rod lenses arranged one behind the other. The optics have an objective lens at their distal end and an eyepiece at their proximal end. The viewer's eye looks through the optics at an observation area that lies in front of the distal end face of the shaft. Alternatively, the optics can also be connected to a digital imaging unit at their proximal end.

It is conceivable for individual components that pass through the shaft part of the resectoscope to be stabilized against one another, particularly counter to a displacement in the radial direction.

To wit, the electrode instrument usually has guide elements that serve to support and stabilize the electrode instrument within the inner tube. For this purpose, the guide elements adjoin the inner wall of the inner tube or of the optics in such a way that movement of the electrode instrument in the axial direction and potentially also rotational movements about the longitudinal axis are possible, while movements of the electrode instrument in the radial direction are reduced or prevented. It has been found to be especially advantageous for the guide elements to be partially complementary in shape to the inner wall. The guide elements can have a partially circular cross section, for instance. Such guide elements are known to those skilled in the art. The guide elements can be made of metal or other materials. The guide elements are especially preferably guide plates. As a rule, no further parts are arranged between the electrode instrument, or the guide elements thereof, and the inner wall of the inner tube. Further components, such as an optical system, for example, can be arranged within the inner tube, however.

As described above, in addition or as an alternative to these guide elements, the insulating insert according to the invention has connecting elements by means of which the electrode instrument is secured radially against displacement while it remains axially movable. It is possible within the scope of the invention to dispense with the usual guide elements described above, since the electrode instrument is guided on the insulating insert. It will readily be understood, however, that additional stabilization by guide elements is also contemplated within the scope of this invention.

The resectoscope shaft generally comprises elements for producing the releasable connection to the insulating insert described elsewhere, particularly for the purpose of releasably connecting the distal end region of the cladding tube or the inner tube to the proximal end region of the insulating insert. These elements are each functionally complementary to the fastening means of the insulating insert described above, so that the elements with the fastening means form a detachable connection between the insulating insert and the resectoscope shaft. The cladding tube or the inner tube of the resectoscope can have an engagement opening for a locking element of the insulating insert in order to form the detachable connection, for example. Alternatively or in addition, the cladding tube or the inner tube can comprise one or more radial protrusions which, in the assembled state, prevent the insulating insert—e.g., an insulating insert having a conical shape—from moving axially in the distal direction.

BRIEF DESCRIPTION OF THE FIGURES

Exemplary embodiments of the invention are shown schematically in the drawings. In the drawing:

FIG. 1 shows a schematic, sectional side view of a resectoscope from the prior art in which an insulating tip is arranged on the inner tube;

FIG. 2 shows a schematic, sectional side view of an alternative resectoscope from the prior art in which an insulating tip is arranged on the cladding tube;

FIG. 6 shows a schematic, sectional side view of the distal end region of an alternative resectoscope according to the invention that has an insulating insert with a conical shape in its proximal end region;

FIG. 7 shows a schematic, sectional side view of the distal end region of an alternative resectoscope according to the invention that has an insulating insert with a conical shape in its proximal end region and in which an electrode instrument is connected in an axially displaceable manner to the insulating insert;

FIG. 8 shows a schematic, sectional side view of the distal end region of an alternative resectoscope according to the invention that has an insulating insert with a conical shape in its proximal end region in which an electrode instrument is connected to the insulating insert in an axially displaceable manner and the insulating insert of which is a locking element for the additional connection between the insulating insert and resectoscope shaft (A) and an enlargement of a section of this sectional view (B)

EXEMPLARY EMBODIMENTS

Additional advantages, characteristics, and features of the present invention will become clear from the following detailed description of exemplary embodiments with reference to the attached drawings. However, the invention is not restricted to these exemplary embodiments.

Figure 3:
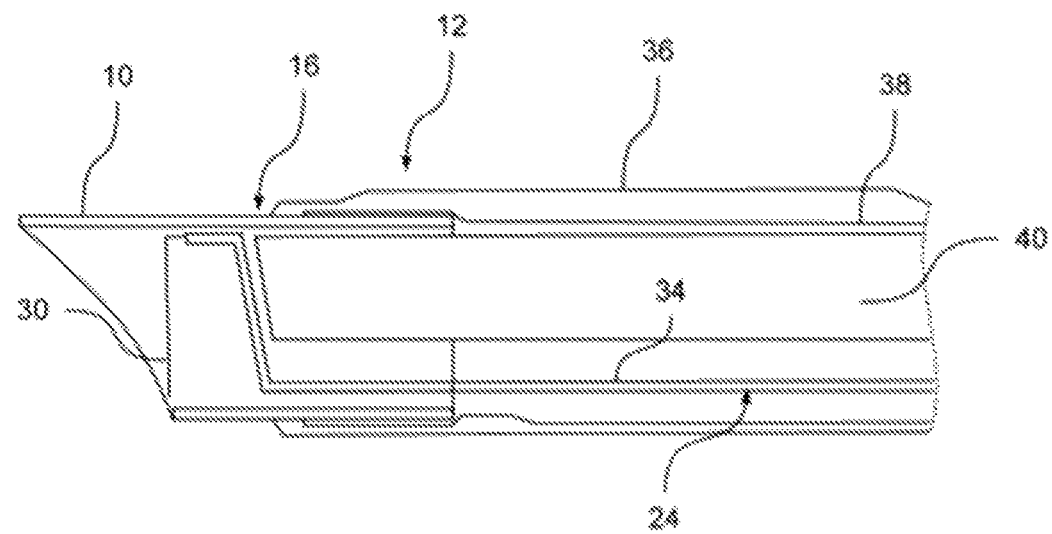
FIG. 3 shows a schematic, sectional side view of the distal end region of the resectoscope from the prior art shown in FIG. 1.

FIG. 1 shows a schematic, sectional side view of a resectoscope 26 from the prior art in which an insulating insert 10 is arranged on the inner tube 38. FIG. 3 shows a schematic, sectional side view of the distal end region of the resectoscope from the prior art.

The resectoscope 26 has a resectoscope shaft 14 that comprises a cladding tube 36 (outer tube), which is shown in dashed lines. An inner tube 38 runs inside the cladding tube 3, and an electrode instrument 24 as well as an optics 40 that is shown in FIG. 3 and an illuminating means, for example in the form of an optical fiber bundle, run inside the inner tube 38. In addition, other elements (not shown here) such as a separate irrigation tube and the like can run in the resectoscopes. In its distal end region, the cladding tube 36 comprises openings (not shown here) through which contaminated irrigation fluid can flow into the space between the cladding tube 36 and the inner tube 38 and can out through the resectoscope shaft 14.

As can be seen in FIG. 1 and in greater detail in FIG. 3, the electrode instrument 24 in this conventional instrument is protected by means of a holding element 46 (guide element) with a partially circular cross section against transverse displacements—meaning displacements that deviate from the longitudinal direction of the resectoscope shaft 14, e.g., transverse to the longitudinal direction. The electrode instrument 24 is supported in a longitudinally displaceable manner in the inner tube 38. The holding element 46 is complementary in shape to the inner wall of the inner tube 38 or to the outer wall of the optics 40 and has a partially cylindrical shape. The holding element 46 is fastened to two fork tubes 34 in a shaft portion of the electrode instrument 24. The fork tubes 34 run closely together within the resectoscope shaft 14 and diverge only in the distal end region of the resectoscope shaft 14 in order to receive and carry a loop electrode between their ends. Alternatively, it is also conceivable for the fork tubes 34 to merge into an electrode instrument shaft tube in the middle or proximal region of the resectoscope 26. In this embodiment, the holding element or elements 46 can be arranged on the electrode instrument shaft tube.

The electrode instrument 24 can be moved in an axially guided manner in the distal and proximal direction through actuation of a handle 48. It can be pushed over the distal end of the inner tube 38 and the cladding tube 36. This enables the surgeon to manipulate tissue that is farther away from the resectoscope tip. For this purpose, the inner tube 38 and/or the electrode instrument 24 are also supported so as to be rotatable about their longitudinal axes. The electrode instrument 24 has at its distal end an electrode 30 that is embodied as a cutting loop and by means of which tissue can be removed by electrosurgical ablation. Here, a high-frequency electrical voltage is applied to the electrode 30 in order to cut tissue.

The resectoscope 26 shown has a passive transporter in which the slide 56 is displaced in the distal direction against the distal, first handle part 52 through a relative movement of the handle parts 50 and 52 that are arranged proximally from the resectoscope shaft 14 against a spring force that is applied by a spring bridge 54. When the slide 56 is displaced in the distal direction against the handle part 52, the electrode instrument 24 is positively guided to the distal in a manner not shown. When the handle parts 50, 52 are released, the spring force generated by the spring bridge 54 forces the slide 56 back into its resting position, the electrode instrument 24 being pulled in the proximal direction. When the slide 56 is moved back, an electrosurgical intervention with the electrode instrument 24 can be carried out without manual force on the part of the surgeon—that is, passively.

In contrast to the insulating insert 10 according to the invention, the insulating insert 10 of this conventional resectoscope 26 is not detachably connected to the resectoscope shaft 14, but rather is permanently fixed to the resectoscope shaft 14 by means of an adhesive bond (not shown here). In addition, the insulating insert 10 also does not include any fastening means 18.

Figure 4:
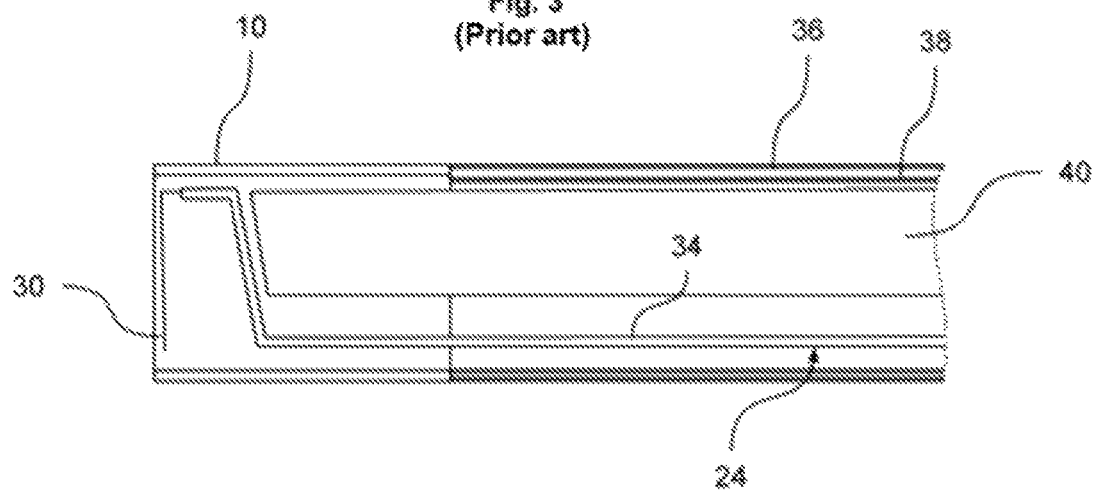
FIG. 4 shows a schematic, sectional side view of the distal end region of the resectoscope from the prior art shown in FIG. 2.

FIG. 2 shows a schematic, sectional side view of an alternative resectoscope 26 from the prior art in which an insulating insert 36 is arranged on the cladding tube 10. FIG. 4 shows a schematic, sectional side view of the distal end region of this known resectoscope 26. By attaching the insulating insert 10 to the cladding tube 36, it is possible to design the resectoscope shaft 14 with an ultra-thin construction. The resectoscope 26 also corresponds substantially to the resectoscope 26 that is shown in FIGS. 1 and 3. In the resectoscope 26 that is shown in FIGS. 2 and 4, the insulating insert 10 and the resectoscope shaft 14 are also connected to one another by permanent gluing.

In contrast to this conventional permanent connection between the insulating insert 10 and the resectoscope shaft 14, FIGS. 5 to 8 show schematic, sectional side views of the distal end region 12 of different resectoscopes 26 in which the connection between the insulating insert 10 and the resectoscope shaft 14 is detachable. Apart from the differences according to the invention described below, the resectoscopes 26 shown are substantially the same as the resectoscopes 26 shown in FIGS. 1 to 4.

Figure 5:
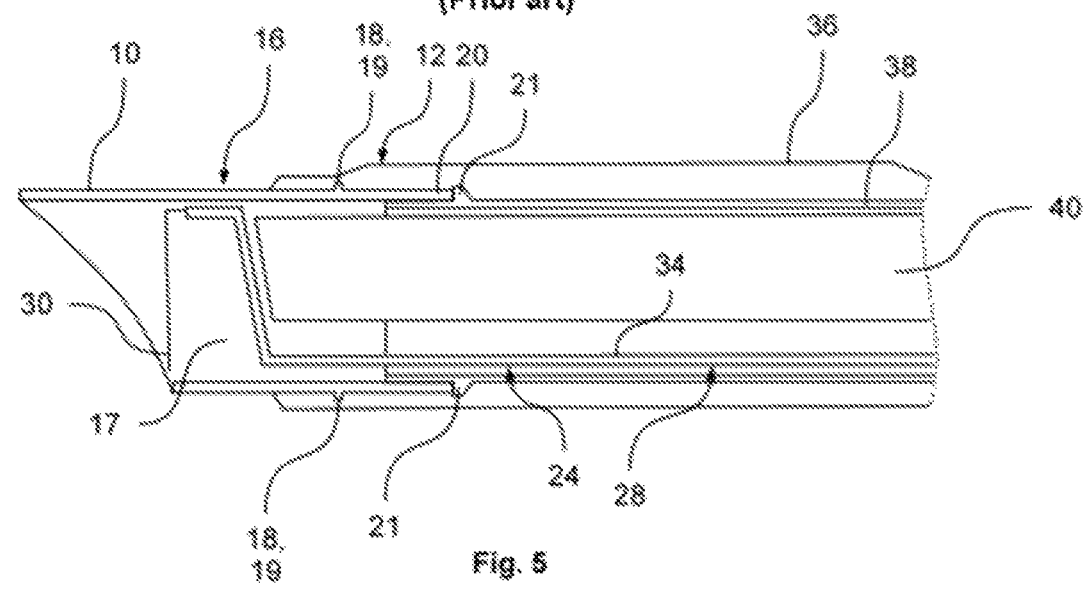
FIG. 5 shows a schematic, sectional side view of the distal end region of a resectoscope according to the invention that has an insulating insert with fastening means arranged radially on the outside.

FIG. 5 shows an embodiment that has an insulating insert with fastening means 18 arranged radially on the outside. The fastening means 18 are embodied as peg-shaped extrusions on the outside of the wall 20 of the insulating insert—i.e., as thickenings 19 of the wall 20. The insulating insert 10 here has more than one fastening means 18, namely at least two fastening means 18, preferably 3, which are arranged in a knob-like manner uniformly along a circumference of the insulating insert 10. It is also conceivable for a single fastening means to be disposed in the form of a circumferential bead on the insulating insert 10 instead. In the embodiment shown here, the inner tube 38 has two or more contact elements 21 with a distal contact surface that can be brought into abutment with the proximal end of the insulating insert 10, thereby preventing the insulating insert 10 from moving in the proximal direction.

FIG. 6 shows an insulating insert 10, the wall 20 of which has a conical shape on the outside in the proximal end region of the insulating insert 10. In other words, the diameter of the insulating insert 10 is larger at its proximal end than at the distal end of its hollow portion 16. It can be seen that the insulating insert 10 is arranged between the cladding tube 38 and the inner tube 36, and that the conically shaped insulating insert 10 is prevented from slipping in the distal direction by a narrowing of the cladding tube 36 at its distal end.

FIG. 7 shows an embodiment in which the resectoscope 26 from FIG. 6 is supplemented by a connection between the insulating insert 10 and the electrode instrument 24. The electrode instrument 24 is connected to the insulating insert 10 so as to be axially displaceable by means of one or more connecting elements 32. Each of the preferably two connecting elements 32 has the shape of a hollow cylinder, the longitudinal axis of the hollow cylinder extending parallel to the longitudinal axis of the resectoscope shaft 14, and a fork tube 34 of the electrode instrument 24 being guided in an axially displaceable manner in the interior of the hollow cylinder.

FIG. 8 shows an embodiment in which the resectoscope 26 from FIG. 7 is supplemented by a additional, detachable connection between insulating insert 10 and resectoscope shaft 14. As will readily be understood, it is also possible within the scope of the invention to dispense with the conical shape of the insulating insert 10 and/or of the connecting element 32 in favor of this additional detachable connection. The insulating insert 10 has a locking element 22 here for producing an additional detachable connection. As can be seen in the enlargement shown in part B of the figure, in this case the locking element 22 is an elongated partial cutout of the inner wall of the insulating insert 10 that is connected to the inner wall of the insulating insert 10. The partial cutout is angled at a flat angle from the inner wall distally toward the inside. The adjacent outer wall of the inner tube 38 has a corresponding engagement opening 42. If the insulating insert 10 is pushed into the position shown over the distal end region of the inner tube 38, the partial cutout comes into engagement with the engagement opening 42. Through exertion of a corresponding tensile force, the insulating insert 10 can be released again and the partial cutout can be broken off in the process.

Figure 9:
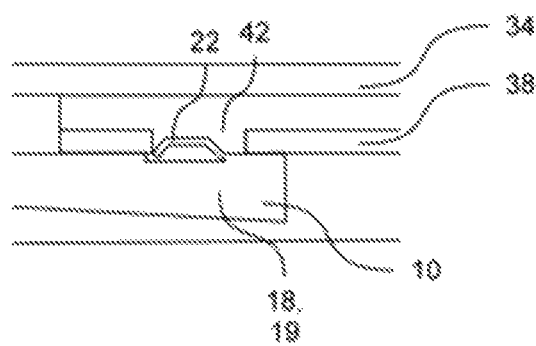
FIG. 9 shows detail of a schematic, sectional side view of the distal end region of another resectoscope according to the invention, the insulating insert of which has a locking member for the additional connection between the insulating insert and the resectoscope shaft, it being possible for the locking connection can be released without destroying the locking element.

Like FIG. 8B, FIG. 9 shows an enlarged section of a resectoscope according to the invention. The insulating insert 10 has a locking element 22 for producing a detachable connection. The locking element 22 is an elongate, partial cutout of the inner wall of the insulating insert 10 that is connected to the inner wall of the insulating insert 10. The partial cutout comprises a proximal portion that is angled inward at a flat angle from the inner wall, a portion that is arranged distally thereof that runs substantially parallel to the longitudinal axis of the resectoscope 26, and a distal portion that is angled outward. The adjacent outer wall of the inner tube 38 has a corresponding engagement opening 42. If the insulating insert 10 is pushed into the position shown over the distal end region of the inner tube 38, the partial cutout comes into engagement with the engagement opening 42. Through exertion of a corresponding tensile force, the insulating insert 10 can be detached again without breaking the partial cutout off. This is ensured in particular by the fact that the locking element 22 has a surface in its distal end region that extends obliquely inward and proximally.

Although the present invention has been described in detail with reference to the exemplary embodiments, it is obvious to those skilled in the art that the invention is not restricted to these exemplary embodiments, but rather that modifications can be made in such a way that individual features are omitted or other combinations of the individual features presented are realized, provided that the scope of protection of the appended claims is not exceeded. The present disclosure includes any and all combinations of the individual features presented.

LIST OF REFERENCE SYMBOLS 10 insulating insert
12 end region
14 resectoscope shaft
16 hollow portion
17 cavity
18 fastening means
19 thickening
20 wall
21 contact elements
22 locking element
24 electrode instrument
26 resectoscope
28 shaft portion
30 electrode
32 connecting element
34 fork tube
36 cladding tube
38 inner tube
40 optics
42 engagement opening
46 holding element
48 handle
50 handle part
52 handle part
54 spring bridge
56 carriage

The invention claimed is:

1. An electrically insulating insert for detachable connection to a distal end region of a resectoscope shaft, the insulating insert comprising:
a hollow portion with an elongate cavity for passage of pass-through instruments, and
a fastening means for detachable connection to the resectoscope shaft, the fastening means comprising:
a radial thickening of the insulating insert in the hollow portion thereof, the radial thickening including a larger outer diameter of the insulating insert relative to an outer diameter at a distal end of the hollow portion,
a part of a bayonet, screw, snap, clamp, or locking connection, and
a protruding locking element that is arranged on a fastening side of the hollow portion and is pointing towards an inside of the hollow portion,
wherein the radial thickening is configured to engage a radially inner surface of the distal end region of the resectoscope to detachably fasten the insulating insert to the resectoscope.

2. The insulating insert as set forth in claim 1, wherein the fastening side of the hollow portion is an outer wall thereof.

3. The insulating insert as set forth in claim 1, wherein the insulating insert is made of plastic.

4. The insulating insert as set forth in claim 3, wherein the plastic is a thermostable plastic.

5. An electrode instrument for use in a resectoscope, the electrode instrument comprising:
a shaft portion, and
an electrode to which high-frequency current can be applied, the electrode being arranged at a distal end of the shaft portion,
wherein the electrode instrument is connected to the insulating insert as set forth in claim 1 and the electrode instrument and the insulating insert can be displaced axially relative to one another.

6. The electrode instrument as set forth in claim 5, wherein the insulating insert comprises one or more connecting elements, in each of which a fork tube of the electrode instrument is supported in an axially displaceable manner.

7. A resectoscope for endoscopic surgery, the resectoscope comprising:
a tubular resectoscope shaft that comprises an elongate cladding tube and an inner tube that is arranged in the cladding tube, as well as rod-shaped optics,
the insulating insert as set forth in claim 1, and
an electrode instrument including a shaft portion and an electrode to which high-frequency current can be applied, the electrode being arranged at a distal end of the shaft portion.

8. The resectoscope as set forth in claim 7, wherein a proximal end region of a wall of the insulating insert is arranged between the cladding tube and the inner tube running inside the cladding tube.

9. The resectoscope as set forth in claim 7, wherein:
the insulating insert is detachably connected to a distal end region of the cladding tube or of the inner tube, and
the cladding tube or the inner tube includes an engagement opening for a locking element of the insulating insert in order to form the detachable connection.

* * * * *